(12) United States Patent
Jairam

(10) Patent No.: US 6,925,849 B2
(45) Date of Patent: Aug. 9, 2005

(54) STAPLER ANVIL

(75) Inventor: Anthony Jairam, Sunrise, FL (US)

(73) Assignee: ACCO Brands, Inc., Lincolnshire, IL (US)

( * ) Notice: Subject to any disclaimer, the term of this patent is extended or adjusted under 35 U.S.C. 154(b) by 0 days.

(21) Appl. No.: 10/238,525

(22) Filed: Sep. 10, 2002

(65) Prior Publication Data

US 2004/0046001 A1 Mar. 11, 2004

(51) Int. Cl.$^7$ .............................................. B21C 3/16
(52) U.S. Cl. ......................... 72/476; 227/155; 227/77; 227/134; 227/61; 227/156; 227/120; 140/93 D
(58) Field of Search .............................. 227/155, 120, 227/77, 84, 85, 134, 61, 156; 72/476; 140/93 D

(56) References Cited

U.S. PATENT DOCUMENTS

| | | | |
|---|---|---|---|
| 2,267,185 A | | 12/1941 | Bauwens |
| 2,667,637 A | | 2/1954 | Marano |
| 2,741,766 A | | 4/1956 | Mott |
| 2,798,219 A | | 7/1957 | Maynard |
| 4,262,836 A | | 4/1981 | Hirose |
| 4,281,785 A | * | 8/1981 | Brooks ........................ 227/120 |
| 4,315,589 A | | 2/1982 | Soong |
| 4,366,924 A | * | 1/1983 | Leiter ........................ 227/155 |
| 4,367,111 A | | 1/1983 | Hirose |
| 4,449,661 A | | 5/1984 | Spehrley, Jr. |
| 4,632,290 A | * | 12/1986 | Green et al. ................ 227/155 |
| 4,778,096 A | | 10/1988 | Ebihara |
| 5,004,142 A | * | 4/1991 | Olesen ........................ 227/155 |
| 5,009,355 A | * | 4/1991 | Akizawa et al. ............. 227/155 |
| 5,029,745 A | * | 7/1991 | Akizawa et al. ............. 227/155 |
| 5,178,314 A | * | 1/1993 | Radtke et al. .............. 227/155 |
| 5,364,000 A | | 11/1994 | Fealey |
| 5,516,025 A | | 5/1996 | Eriksson |
| 5,678,745 A | * | 10/1997 | Yoshie ........................ 227/155 |
| 5,791,548 A | | 8/1998 | Udagawa et al. |
| 5,799,935 A | | 9/1998 | Yamanushi et al. |
| 6,056,183 A | * | 5/2000 | Tanabe ........................ 227/155 |
| 6,244,491 B1 | | 6/2001 | Kandasamy et al. |

* cited by examiner

*Primary Examiner*—Louis K. Huynh
*Assistant Examiner*—Michelle Lopez
(74) *Attorney, Agent, or Firm*—Michael Best & Friedrich LLP

(57) ABSTRACT

A stapler anvil and method for clinching a staple is disclosed. The anvil includes a body having a well. The well has an axis extending between the legs of a staple and is defined by a first surface having a first portion along which the first leg of the staple is directed as the staple is being clinched, and a second portion extending substantially at an angle relative to the first portion to direct the second leg of the staple at least partially away from the axis as the staple is clinched. The well is further defined by a second surface spaced from the first surface. The second surface is configured to redirect the second leg of the staple at least partially back toward the axis after the second leg has been directed at least partially away from the axis by the second portion of the first surface.

9 Claims, 2 Drawing Sheets

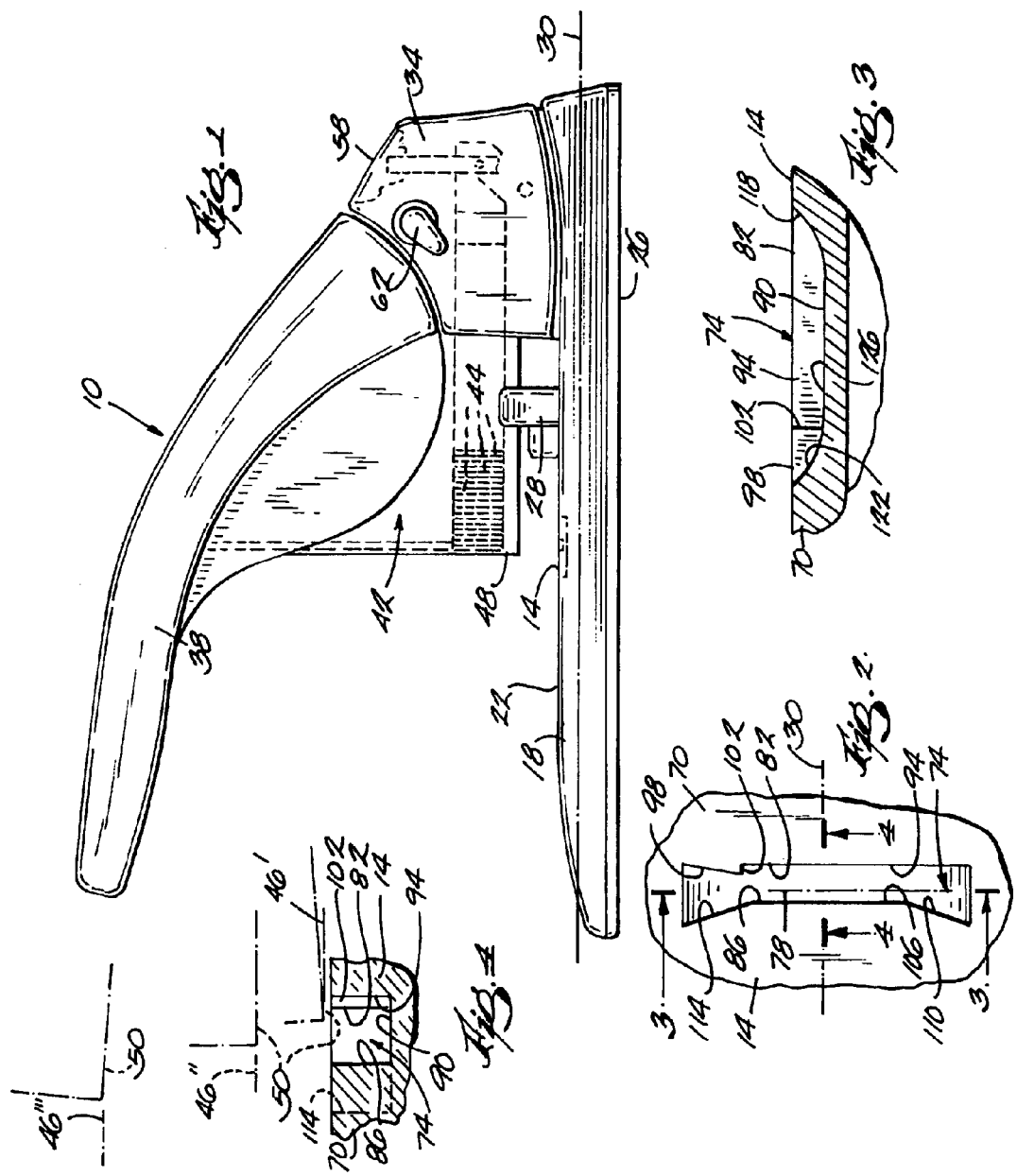

STAPLER ANVIL

FIELD OF THE INVENTION

The invention relates to staplers, and more particularly to anvils used for clinching staples.

BACKGROUND OF THE INVENTION

Manually-operated staplers typically include a base that supports a stationary anvil. The anvil is configured to receive and clinch the legs of a staple after passing through the sheets being stapled.

Prior art stationary anvils are commonly designed to accommodate a single size of staple used in the specific stapler on which the anvil is mounted. A typical stapler is capable of successfully fastening together a predetermined range of total sheets. For example, many light-use, desktop staplers accommodate a single size of staple and will staple from two to about twenty sheets successfully. Attempts to staple more sheets will often be unsuccessful because the staple legs are not long enough to accommodate more than about twenty sheets.

Larger, heavy-duty staplers use longer staples designed to staple more sheets. The anvils of heavy-duty staplers are designed to clinch staple legs that have passed through a relatively large number of sheets. Attempts to staple only a relatively small number of sheets (e.g., about twenty sheets) with a heavy-duty stapler will often be unsuccessful because the long legs of the staple will hit one another, jam, and prevent the staple from being completely driven by the stapler. To eliminate or reduce the occurrence of jamming when stapling larger numbers of sheets, the user is required to manually change the staple sizes for different stapling jobs.

SUMMARY OF THE INVENTION

The present invention provides an improved stapler anvil designed for use on a stapler that can successfully fasten from about twenty to about 120–150 sheets using only one size of staple. The anvil substantially prevents staple jamming when stapling a small number of sheets by allowing the legs to bypass one another. After the legs bypass one another, the anvil guides the bypassed legs at least partially back together to obtain a clinch that facilitates staple removal and that is aesthetically pleasing. When stapling a larger number of sheets, where no leg bypass is needed to prevent jamming, the anvil guides the legs in a different manner to clinch the legs.

More specifically, the invention provides a stapler anvil for clinching a staple having a first leg and a second leg. The anvil includes a body and a well in the body. The well has an axis extending between an insertion point of the first leg and an insertion point of the second leg and is defined by a first surface having a first portion along which the first leg of the staple is directed as the staple is being clinched, and a second portion extending substantially at an angle relative to the first portion to direct the second leg of the staple at least partially away from the axis as the staple is being clinched. The well is further defined by a second surface spaced from the first surface. The second surface is configured to redirect the second leg of the staple at least partially back toward the axis after the second leg has been directed at least partially away from the axis by the second portion of the first surface.

In one aspect of the invention, the first portion is substantially parallel to the axis and the second surface includes a first portion that is substantially parallel to the axis so that the second leg of the staple is redirected at least partially back toward the axis to be at least partially substantially parallel to the axis. The first portion of the second surface includes opposite ends, and a second portion extends from one of the opposite ends in a direction away from the axis, and a third portion extends from the other of the opposite ends in a direction away from the axis.

The invention also provides a stapler anvil configured for use with a stapler capable of stapling a range of sheets with a single size staple having a first leg and a second leg. The anvil includes a body and a well in the body. The well is defined by a first set of surfaces that cooperates to clinch the staple in a first configuration when the stapler is stapling a first fractional portion of the range of sheets, and a second set of surfaces that cooperates to clinch the staple in a second configuration when the stapler is stapling a second fractional portion of the range of sheets.

In one aspect of the invention, the well has an axis extending between an insertion point of the first leg and an insertion point of the second leg, and the first configuration includes the first leg being substantially coaxial with the axis and the second leg being at least partially offset from the axis. The second leg has a first portion bent away from the axis and a second portion bent back toward the axis. The second fractional portion of the range of sheets includes more sheets than the first fractional portion of the range of sheets.

In another aspect of the invention, the well is further defined by a third set of surfaces that cooperates to clinch the staple in a third configuration when the stapler is stapling a third fractional portion of the range of sheets. The third fractional portion of the range of sheets includes more sheets than both the first and second fractional portions of the range of sheets. The range of sheets is from about twenty to about 120–150 sheets.

The invention further provides a method of clinching a staple having a first leg and a second leg. The method includes inserting the legs into a well in an anvil, the inserted legs defining an axis extending between an insertion point of the first leg and an insertion point of the second leg, bending the first leg, bending the second leg at least partially away from the axis, and subsequent to bending the second leg at least partially away from the axis, bending the second leg at least partially back toward the axis.

In one aspect of the invention, bending the first leg includes bending the first leg in a direction substantially parallel to the axis. In another aspect of the invention, bending the second leg at least partially away from the axis includes guiding the second leg along a surface that is angled with respect to the axis, and bending the second leg at least partially back toward the axis includes guiding the second leg along a surface that is substantially parallel to the axis.

The invention also provides a method of clinching staples in a stapler having an anvil with a well. Each staple has a first leg and a second leg and is capable of stapling a range of sheets. The method includes inserting a first fractional portion of the range of sheets into the stapler, inserting the legs of a first staple through the first fractional portion of the range of sheets and into the well, using a first set of surfaces that defines a portion of the well to clinch the legs of the first staple in a first configuration, and removing the stapled first fractional portion of the range of sheets from the stapler. The method further includes inserting a second fractional portion of the range of sheets into the stapler, inserting the legs of a second staple through the second fractional portion of the range of sheets and into the well, and using a second set of surfaces that defines a portion of the well to clinch the legs of the second staple in a second configuration that is different from the first configuration.

In one aspect of the invention, the method further includes removing the stapled second fractional portion of the range of sheets from the stapler, inserting a third fractional portion of the range of sheets into the stapler, inserting the legs of a third staple through the third fractional portion of the range of sheets and into the well, and using a third set of surfaces that defines a portion of the well to clinch the legs of the third staple in a third configuration.

Other features and advantages of the invention will become apparent to those skilled in the art upon review of the following detailed description, claims, and drawings.

BRIEF DESCRIPTION OF THE DRAWINGS

FIG. 1 is a side view of a stapler having an anvil embodying the invention.

FIG. 2 is partial top view of the anvil shown in FIG. 1.

FIG. 3 is a cross-sectional view taken through line 3—3 of FIG. 2.

FIG. 4 is a cross-sectional view taken through line 4—4 of FIG. 2.

Figure 5:
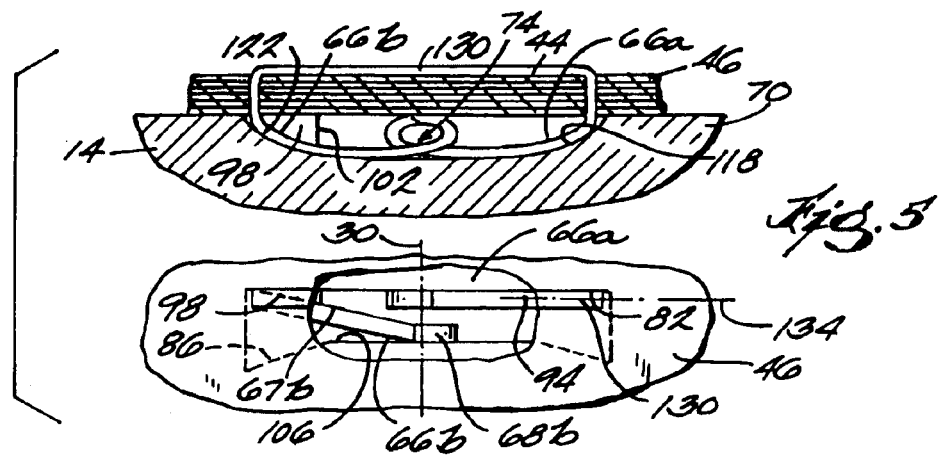
FIG. 5 includes a cross-sectional view and the corresponding partially broken-away top view illustrating a staple clinched in a first configuration by the anvil shown in FIG. 1.

Before one embodiment of the invention is explained in detail, it is to be understood that the invention is not limited in its application to the details of construction and the arrangements of the components set forth in the following description or illustrated in the drawings. The invention is capable of other embodiments and of being practiced or being carried out in various ways. Also, it is understood that the phraseology and terminology used herein is for the purpose of description and should not be regarded as limiting. The use of "including" and "comprising" and variations thereof herein is meant to encompass the items listed thereafter and equivalents thereof as well as additional items.

DETAILED DESCRIPTION OF THE PREFERRED EMBODIMENT

FIG. 1 illustrates a stapler 10 including an anvil 14 embodying the invention. The stapler 10 includes a base 18 having a top surface 22 and a bottom surface 26. The top surface 22 is configured to support a stack of sheets to be stapled. An adjustable paper guide 28 is mounted on the top surface 22. The bottom surface 26 is configured to support the stapler 10 on a support surface. The base 18 defines a longitudinal axis 30.

The base 18 includes an upper housing 34 that houses components of the stapling mechanism. A lever arm 38 is movably coupled (e.g., pivotally) to the base 18. A magazine assembly 42 is coupled with the upper housing 34 and the lever arm 38, and operates to discharge a staple 44 into a plurality of sheets 46 (see FIGS. 5–7) upon manual actuation of the lever arm 38. The magazine assembly 42 includes a magazine 48 that holds a row of staples 44. The magazine 48 includes a discharge opening (not shown) through which a staple 44 is discharged from the magazine 48 into the sheets 46.

The magazine 48 can be opened via a magazine release button 58 located on the upper housing 34. When the magazine release button 58 is depressed, the magazine 48 slides relative to the remainder of the magazine assembly 42 in the direction of the longitudinal axis 30 and away from the upper housing 34. In the open position, the magazine 48 can be refilled with staples 44. To close the magazine 48, the user pushes the magazine 48 toward the upper housing 34.

The stapler 10 further includes a jam clearing mechanism operated by a jam clearing lever 62. In the illustrated embodiment, the jam clearing lever 62 is rotatable with respect to the upper housing 34. When the magazine 48 is jammed with a staple 44, the user manually rotates the jam clearing lever 62 one or more times until the jammed staple is cleared.

The anvil 14 is coupled to the top surface 22 of the base 18 with any suitable fasteners, such as screws, rivets, adhesives, etc. (not shown), and is configured to receive the legs 66a and 66b (see FIGS. 5–7) of a staple 44 dispensed from the magazine 48. When the legs 66a, 66b of the staple engage the anvil 14, they are bent and clinched, as will be described in greater detail below.

FIGS. 2–4 illustrate the anvil 14 in greater detail. The anvil 14 includes a body 70 made from a hard material, such as metal. A well or recess 74 is defined in the body 70. The well 74 includes a lateral axis 78 (see FIG. 2) extending substantially normal to the longitudinal axis 30 and is defined by a first surface or sidewall 82 extending generally in the lateral direction, a second surface or sidewall 86 spaced from the first sidewall 82 and extending generally in the lateral direction, and a third surface or floor 90 that extends between the first and second sidewalls 82, 86. Any suitable fabrication techniques, such as machining, stamping, forging, etc., can be used to form the well 74.

In the illustrated embodiment, the anvil 14 is coupled to the stapler so that the first sidewall 82 is nearest to the paper guide 28 and the upper housing 34. The first sidewall 82 includes a first portion 94 that extends substantially parallel to the lateral axis 78, a second portion 98 that extends substantially at an angle relative to the first portion 94, and a third portion 102 interconnecting the first and second portions 94, 98. In the illustrated embodiment, the second portion 98 is angled about seven degrees from the first portion 94. However, the angle can vary depending on the size of staple being used. A range of about five degrees to about nine degrees is believed to be satisfactory. The third portion 102 is illustrated as being substantially normal to the lateral axis 78 to define a step between the first and second portions 94 and 98, but this need not be the case. Instead, the third portion 102 can interconnect the first and second portions 94 and 98 at different angles.

The second sidewall 86 includes a first portion 106 that extends substantially parallel to the lateral axis 78, a second portion 110 that extends from one of the opposite ends of the first portion 106 in a direction away from the lateral axis 78, and a third portion 114 that extends from the other of the opposite ends of the first portion 106 in a direction away from the lateral axis 78. In the illustrated embodiment, the first portion 106 of the second sidewall 86 is spaced longitudinally about 1.80 mm from the first portion 94 of the first sidewall 82. The longitudinal spacing between the first portion 94 of the first sidewall 82 and the second and third portions 110 and 114 of the second sidewall 86 increases from about 1.80 mm, adjacent the ends of the first portion 106 of the second sidewall 86, to about 3.00 mm adjacent the laterally-outermost ends of the second and third portions 110 and 114 of the second sidewall 86. As with all of the dimensions specified herein, these dimensions can vary depending on the size of the staple being used and the range of sheets the stapler can accommodate.

The floor 90 includes opposite lateral end portions 118, 122 configured to receive and initiate bending of the staple legs 66a, 66b. In the illustrated embodiment, the floor 90 extends laterally a total distance of about 15.60 mm. The end portions 118, 122 curve toward a central portion 126 that extends substantially parallel to the top surface 22 between the curved end portions 118, 122. The specific radius of curvature of the end portions 118, 122 can be varied to achieve the proper initial bending/curling of the staple legs 66a, 66b, and in the illustrated embodiment, the radius of curvature is approximately 4.2 mm. While the central portion 126 is illustrated and described as being substantially parallel to the top surface 22, the central portion can alternatively curve upwardly toward an apex (not shown) positioned near the center of the central portion 126 to facilitate curling the staple legs 66a, 66b back toward the sheets 46 being stapled. In the illustrated embodiment, however, such an apex is not required to achieve the desired curling of the staple legs 66a, 66b.

The longitudinal spacing between the first and second sidewalls 82 and 86 is selected to accommodate stapling a relatively large range of sheets 46. In the illustrated embodiment the range of sheets to be stapled is from about twenty to about 150 sheets, and more preferably from about twenty to about 120 sheets. Referring to FIG. 4, it can be seen how the number of sheets 46 being stapled affects the longitudinal position in which the staple legs 66a, 66b enter the well 74. It is to be understood that FIG. 4 is shown for illustrative purposes only and is not drawn to scale. The specific orientation of the magazine 48 with respect to the well 74 in the illustrated stapling positions will vary depending on the specific stapler and the thickness of the sheets being stapled.

The thickness of standard sheet of copy paper is approximately 0.10 mm. When stapling only about twenty sheets, the thickness of the stack of sheets 46 will be about 2.0 mm. The bottom surface 50 (as represented on the lower right phantom-line magazine 48 in FIG. 4) will follow its arcuate path downward into engagement with the sheets 46'. Because the stack of sheets 46' is relatively small, the location of the staple discharge opening is such that the staple legs 66a, 66b will enter the well 74 closely adjacent the first sidewall 82. The staple clinching action for this situation will be described below with respect to FIG. 5.

Still referring to FIG. 4, when stapling about sixty sheets, the thickness of the stack of sheets 46" will be about 6.0 mm. The bottom surface 50 (as represented on the middle phantom-line magazine 48 in FIG. 4) will follow its arcuate path downward into engagement with the sheets 46". Because the stack of sheets 46" is larger than the stack 46', the location of the staple discharge opening is such that the staple legs 66a, 66b will enter the well 74 at a point about midway between the first and second sidewalls 82 and 86. The staple clinching action for this situation will be further described below with respect to FIG. 6.

Still referring to FIG. 4, when stapling about 120 sheets, the thickness of the stack of sheets 46''' will be about 12.0 mm. The bottom surface 50 (as represented on the upper left phantom-line magazine 48) will follow its arcuate path downward into engagement with the sheets 46'''. Because the stack of sheets 46''' is larger than the stack 46", the location of the staple discharge opening is such that the staple legs 66a, 66b will enter the well 74 closely adjacent the second sidewall 86. The staple clinching action for this situation will be further described below with respect to FIG. 7.

The staple 44 includes a crown 130 that extends between the legs 66a, 66b. In the illustrated embodiment, the crown 130 is about 13.33 mm long and the legs 66a, 66b are each about 15.88 mm long. The staple 44 is about 0.56 mm wide (in the longitudinal direction) and about 0.46 mm thick (in the lateral direction with respect to the legs 66a, 66b). The distal ends of the legs 66a, 66b preferably include a chamfer of about 45 degrees.

The clinching action created by the anvil 14 will now be described with reference to the three exemplary stapling situations depicted in FIGS. 5–7. FIG. 5 illustrates a situation where a relatively small fractional portion (e.g., about twenty sheets) of the total range of sheets that can be accommodated by the stapler 10 is being stapled. The legs 66a, 66b enter the well 74 closely adjacent the first sidewall 82. Upon entering the well 74 in this position, the staple will be clinched using a combination or set of well surfaces (specified below) to achieve a final clinched configuration. A staple axis 134 is defined in the well 74 between the insertion points of the legs 66a, 66b. In the illustrated embodiment, the staple axis 134 defined in the well 74 is substantially parallel to the lateral axis 78 of the well 74.

As the leg 66a enters the well 74, the distal end of the leg 66a engages the end portion 118 of the floor 90 and initially bends toward the longitudinal axis 30 and curls back toward the sheets 46. As the staple 44 is driven further into the well 74, the leg 66a is directed and guided toward the longitudinal axis 30 in a direction substantially parallel to the staple axis 134 by the first portion 94 of the first sidewall 82. When the staple 44 is completely clinched, the leg 66a will be substantially coaxial with the staple axis 134 and the distal end of the leg 66a will be in close proximity to the third portion 102 of the first sidewall 82.

As the leg 66b enters the well 74, the distal end of the leg 66b engages the end portion 122 of the floor 90 and initially bends toward the longitudinal axis 30 and curls back toward the sheets 46. As the staple 44 is driven further into the well 74, the leg 66b is directed and guided at least partially toward the longitudinal axis 30 in a direction at least partially away from the staple axis 134 by the second portion 98 of the first sidewall 82. As used herein and in the appended claims, the phrases "at least partially toward" and "at least partially away" mean that at least one component of a directional vector along which a staple leg is travelling is oriented toward or away, respectively, from the stated reference object or point. The second portion 98 of the first sidewall 82 thereby causes the leg 66b to bypass the leg 66a by directing the leg 66b off the staple axis 134.

As the leg 66b is driven further into the well 74, the distal end of the leg 66b is directed by the second portion 98 of the first sidewall 82 into engagement with the first portion 106 of the second sidewall 86, which operates to re-direct and guide the leg 66b at least partially back toward the staple axis 134. As used herein and in the appended claims, the phrase "at least partially back toward" means that the directional vector along which a portion of a staple leg is currently travelling is oriented more toward the stated reference object or point than the directional vector along which the same portion of the staple leg was previously travelling. The first portion 106 of the second sidewall 86 thereby re-directs the leg 66b from the bypassing path defined by the second portion 98 of the first sidewall 82 back to a substantially parallel, yet offset orientation with respect to the leg 66a and the staple axis 134. As a result, the leg 66b has a first portion 67b bent at least partially away from the staple axis 134 and a second portion 68b bent at least partially back toward the staple axis 134. This provides for an aesthetically-pleasing, final clinched configuration (see FIG. 5) that also facilitates staple removal.

Figure 6:
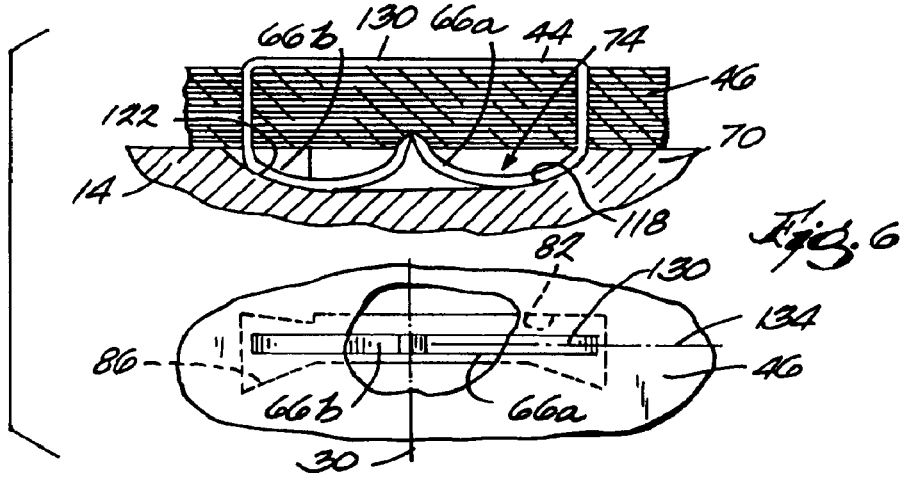
FIG. 6 includes a cross-sectional view and the corresponding partially broken-away top view illustrating a staple clinched in a second configuration by the anvil shown in FIG. 1.

FIG. 6 illustrates a situation where a relatively larger fractional portion (e.g., about sixty sheets) of the total range of sheets that can be accommodated by the stapler 10 is being stapled. As described above with respect to FIG. 4, because there are more sheets 46 being stapled, the legs 66a, 66b enter the well 74 at a point about midway between the first and second sidewalls 82 and 86. Upon entering the well 74 in this position, the staple will be clinched in a different manner, using a different combination or set of well surfaces (specified below), to achieve a different final configuration from that described above with respect to FIG. 5.

Specifically, as the legs 66a, 66b enter the well 74, the distal ends of each leg engage the respective end portions 118, 122 of the floor 90 and are bent toward the longitudinal axis 30 and curled back toward the sheets 46. As the staple 44 is driven further, each leg 66a, 66b travels toward the longitudinal axis 30 on a path substantially coaxial with the staple axis 134 until the staple 44 reaches the final clinched position illustrated in FIG. 6. Note that the distal ends of the legs 66a, 66b may pierce and re-enter the stack of sheets 46 (e.g., into about five or six sheets) from the bottom side. Because the staple legs 66a, 66b have passed through a larger stack of sheets 46, a shorter length of each leg 66a, 66b is clinched. The shorter length of the legs being clinched allows the legs 66a, 66b to be clinched in the manner shown in FIG. 6 without fear that the distal ends of the legs 66a, 66b will engage one another, jam, and cause problems with the stapling process. Therefore, there is no need to have one of the legs 66a, 66b bypass the other as described and illustrated above with respect to FIG. 5.

Figure 7:
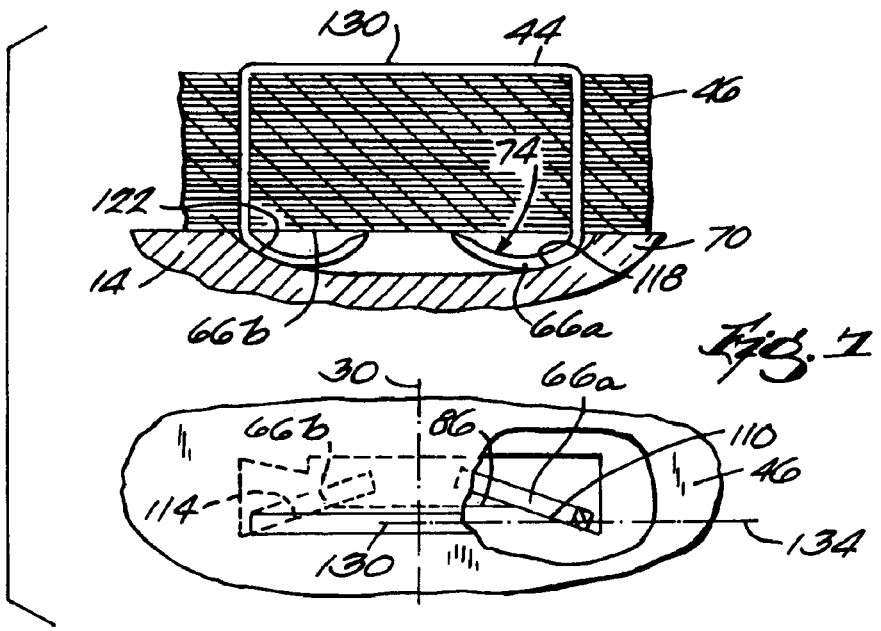
FIG. 7 includes a cross-sectional view and the corresponding partially broken-away top view illustrating a staple clinched in a third configuration by the anvil shown in FIG. 1.

FIG. 7 illustrates a situation where an even larger fractional portion (e.g., about 120–150 sheets) of the total range of sheets that can be accommodated by the stapler 10 is being stapled. As described above with respect to FIG. 4, because there are more sheets 46 being stapled, the legs 66a, 66b enter the well 74 closely adjacent the second sidewall 86. Upon entering the well 74 in this position, the staple will be clinched in a different manner, using a different combination or set of well surfaces (specified below), to achieve yet a different final configuration from that described above with respect to FIGS. 5 and 6.

Specifically, as the legs 66a, 66b enter the well 74, the distal ends of each leg engage the respective end portions 118, 122 of the floor 90 adjacent the respective second and third portions 110, 114 of the second sidewall 86 and are initially bent toward the longitudinal axis 30 and curled back toward the sheets 46. As the staple 44 is driven further, each leg 66a, 66b is guided along the respective second and third portions 110, 114 of the second sidewall 86 in a direction at least partially toward the longitudinal axis 30 on a path at least partially away from the staple axis 134 until the staple 44 reaches the final clinched position illustrated in FIG. 7. Because the staple legs 66a, 66b have passed through a larger stack of sheets 46, a shorter length of each leg 66a, 66b is clinched. The shorter length of the legs being clinched allows the legs 66a, 66b to be clinched in the manner shown in FIG. 7 without fear that the distal ends of the legs 66a, 66b will engage one another, jam, and cause problems with the stapling process. Therefore, there is again no need to have one of the legs 66a, 66b bypass the other as described and illustrated above with respect to FIG. 5.

Those skilled in the art will understand that the staple positions and clinched configurations illustrated in FIGS. 5–7 are illustrative of specific stapling situations that will vary depending on the size of the staple 44, the specific configuration of the well 74, the number and thickness of sheets 46 being stapled, and the manner in which the magazine 48 pivots with respect to the anvil 14. Other staple positions and clinched configurations will result when stapling conditions change. For example, there will be stapling situations where the resulting staple position and clinched configuration will fall somewhere between the configurations shown in FIG. 5 and FIG. 6, and somewhere between the configurations shown in FIG. 6 and FIG. 7.

Those skilled in the art will also understand that the illustrated configuration of the well 74 can be varied to some extent (beyond the variations already discussed above) without deviating from the scope of the invention. For example, the second and third portions 110 and 114 of the second sidewall 86 need not extend at the illustrated angle away from the first portion 106 of the second sidewall 86. Instead, the second and third portions 110 and 114 of the second sidewall 86 can be configured in other suitable ways as long as they provide an area of the well 74 suitable for receiving the legs 66a, 66b when a relatively large stack of sheets 46 is being stapled. For example, instead of extending at angles from the opposite ends of the first portion 106 of the second sidewall 86, the second and third portions 110 and 114 could be substantially parallel to and offset from the first portion 106 of the second sidewall 86 in a direction away from the first sidewall 82. Respective interconnecting portions (not shown) would then provide a step or transition between the second and third portions 110, 114 and the first portion 106 of the second sidewall 86. Of course, changing the configuration of the well 74 in this manner would result in a clinched configuration different from that described above with respect to FIG. 7.

Additionally, those skilled in the art will understand that the first, second, and third portions 94, 98, and 102 of the first sidewall 82 could be oriented in mirror-relation about the longitudinal axis 30 from the orientation shown. In other words, the second and third portions 98 and 102 could be located opposite the second portion 110 of the second sidewall 86, instead of in their illustrated location opposite the third portion 114 of the second sidewall 86. If this change were made, the clinching operation described above with respect to FIG. 5 would occur in substantially the same manner except that the actions of the legs 66a and 66b would be reversed.

Various features of the invention are set forth in the following claims.

What is claimed is:

1. A method of clinching a staple having a first leg and a second leg, the method comprising:
   inserting the legs into a well in an anvil, the well being defined by stationary surfaces, the inserted legs defining an axis extending between an insertion point of the first leg and an insertion point of the second leg;
   bending the first leg;
   bending the second leg at least partially away from the axis due to engagement of the second leg with a first one of the stationary surfaces; and subsequent to bending the second leg at least partially away from the axis, bending the second leg at least partially back toward the axis due to engagement of the second leg with a second one of the stationary surfaces.

2. The method of claim 1, wherein bending the first leg includes bending the first leg in a direction substantially parallel to the axis.

3. The method of claim 1, wherein bending the second leg at least partially away from the axis includes guiding the second leg along the first one of the stationary surfaces that is angled with respect to the axis.

4. The method of claim 1, wherein bending the second leg at least partially back toward the axis includes guiding the second leg along the second one of the stationary surfaces that is substantially parallel to the axis.

5. A method of clinching staples in a stapler having an anvil with a well defined by stationary surfaces and no moving parts, each staple having a first leg and a second leg and being capable of stapling a range of sheets, the method comprising:

inserting a first fractional portion of the range of sheets into the stapler;

inserting the legs of a first staple through the first fractional portion of the range of sheets and into the well;

using a first set of stationary surfaces that defines a portion of the well to clinch the legs of the first staple in a first configuration;

removing the stapled first fractional portion of the range of sheets from the stapler;

inserting a second fractional portion of the range of sheets into the stapler, the second fractional portion being different from the first fractional portion;

inserting the legs of a second staple through the second fractional portion of the range of sheets and into the well; and using a second set of stationary surfaces that defines a portion of the well to clinch the legs of the second staple in a second configuration, the second set of stationary surfaces being different from the first set of stationary surfaces and the second configuration being different from the first configuration.

6. The method of claim 5, wherein the well has an axis extending between an insertion point of the first leg and an insertion point of the second leg of the first staple, and wherein clinching the first staple in the first configuration includes:

bending the first leg in a direction substantially parallel to the axis;

bending the second leg at least partially away from the axis due to engagement of the second leg with one of the stationary surfaces in the first set of stationary surfaces; and subsequent to bending the second leg at least partially away from the axis, bending the second leg at least partially back toward the axis due to engagement of the second leg with another of the stationary surfaces in the first set of stationary surfaces.

7. The method of claim 6, wherein bending the second leg at least partially away from the axis includes guiding the second leg along a stationary surface that is angled with respect to the axis.

8. The method of claim 6, wherein bending the second leg at least partially back toward the axis includes guiding the second leg along a stationary surface that is substantially parallel to the axis.

9. The method of claim 5, further including:

removing the stapled second fractional portion of the range of sheets from the stapler;

inserting a third fractional portion of the range of sheets into the stapler, the third fractional portion being different from the first fractional portion and the second fractional portion;

inserting the legs of a third staple through the third fractional portion of the range of sheets and into the well;

using a third set of stationary surfaces that defines a portion of the well to clinch the legs of the third staple in a third configuration, the third set of stationary surfaces being different from the first set of stationary surfaces and the second set of stationary surfaces, and the third configuration being different from the first configuration and the second configuration.

* * * * *